United States Patent
Schmitt et al.

(10) Patent No.: US 8,753,281 B2
(45) Date of Patent: *Jun. 17, 2014

(54) OPTO-ACOUSTIC IMAGING DEVICES AND METHODS

(75) Inventors: Joseph M. Schmitt, Andover, MA (US); Christopher Petersen, Carlisle, MA (US); Toro Ohasi, Aichi (JP); Tetsuya Nakamatsu, Arlington, MA (US)

(73) Assignee: Lightlab Imaging Inc., Westford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/618,520

(22) Filed: Sep. 14, 2012

(65) Prior Publication Data

US 2013/0012811 A1    Jan. 10, 2013

Related U.S. Application Data

(60) Continuation of application No. 13/051,567, filed on Mar. 18, 2011, now Pat. No. 8,449,468, which is a division of application No. 11/983,417, filed on Nov. 8, 2007, now Pat. No. 7,935,060.

(60) Provisional application No. 60/857,573, filed on Nov. 8, 2006.

(51) Int. Cl.
*A61B 8/14* (2006.01)
*A61B 6/00* (2006.01)

(52) U.S. Cl.
USPC ............................................ 600/467; 600/476

(58) Field of Classification Search
USPC ................... 600/407, 443, 467, 476; 356/477
See application file for complete search history.

(56) References Cited

U.S. PATENT DOCUMENTS

| 5,076,279 | A | 12/1991 | Arenson et al. |
| 5,274,551 | A | 12/1993 | Corby, Jr. |
| 5,293,873 | A | 3/1994 | Fang |
| 5,313,949 | A | 5/1994 | Yock |
| 5,321,501 | A | 6/1994 | Swanson et al. |

(Continued)

FOREIGN PATENT DOCUMENTS

| JP | 11-056752 | 3/1999 |
| JP | 2002-153472 | 5/2002 |

(Continued)

OTHER PUBLICATIONS

International Search Report and the Written Opinion of the International Searching Authority for International Application No. PCT/US2007/023493 issued on Apr. 23, 2008.

(Continued)

*Primary Examiner* — Michael Rozanski
(74) *Attorney, Agent, or Firm* — K&L Gates LLP (57) ABSTRACT

In one aspect, the invention relates to a probe. The probe includes a sheath, a flexible, bi-directionally rotatable, optical subsystem positioned within the sheath, the optical subsystem comprising a transmission fiber, the optical subsystem capable of transmitting and collecting light of a predetermined range of wavelengths along a first beam having a predetermined beam size. The probe also includes an ultrasound subsystem, the ultrasound subsystem positioned within the sheath and adapted to propagate energy of a predetermined range of frequencies along a second beam having a second predetermined beam size, wherein a portion of the first and second beams overlap a region during a scan.

14 Claims, 10 Drawing Sheets

(56) References Cited

U.S. PATENT DOCUMENTS

| | | |
|---|---|---|
| 5,335,662 A | 8/1994 | Kimura et al. |
| 5,350,377 A | 9/1994 | Winston et al. |
| 5,459,570 A | 10/1995 | Swanson et al. |
| 5,465,147 A | 11/1995 | Swanson |
| 5,509,093 A | 4/1996 | Miller et al. |
| 5,582,178 A | 12/1996 | Yock |
| 5,588,434 A | 12/1996 | Fujimoto |
| 5,619,368 A | 4/1997 | Swanson |
| 5,748,598 A | 5/1998 | Swanson et al. |
| 5,784,352 A | 7/1998 | Swanson et al. |
| 5,830,145 A | 11/1998 | Tenhoff |
| 5,956,355 A | 9/1999 | Swanson et al. |
| 6,111,645 A | 8/2000 | Tearney et al. |
| 6,129,667 A | 10/2000 | Dumoulin et al. |
| 6,134,003 A | 10/2000 | Tearney et al. |
| 6,160,826 A | 12/2000 | Swanson et al. |
| 6,191,862 B1 | 2/2001 | Swanson et al. |
| 6,217,527 B1 | 4/2001 | Selmon et al. |
| 6,226,546 B1 | 5/2001 | Evans |
| 6,265,792 B1 | 7/2001 | Granchukoff |
| 6,282,011 B1 | 8/2001 | Tearney et al. |
| 6,299,622 B1 | 10/2001 | Snow et al. |
| 6,421,164 B2 | 7/2002 | Tearney et al. |
| 6,423,002 B1 | 7/2002 | Hossack |
| 6,445,939 B1 | 9/2002 | Swanson et al. |
| 6,485,413 B1 | 11/2002 | Boppart et al. |
| 6,501,551 B1 * | 12/2002 | Tearney et al. ............ 356/477 |
| 6,552,796 B2 | 4/2003 | Magnin et al. |
| 6,564,087 B1 | 5/2003 | Pitris et al. |
| 6,570,659 B2 | 5/2003 | Schmitt |
| 6,585,660 B2 | 7/2003 | Dorando et al. |
| 6,706,004 B2 | 3/2004 | Tearney et al. |
| 6,847,454 B2 | 1/2005 | Crowley et al. |
| 6,879,851 B2 | 4/2005 | McNamara et al. |
| 6,891,984 B2 | 5/2005 | Petersen et al. |
| 6,947,787 B2 | 9/2005 | Webler |
| 7,134,994 B2 | 11/2006 | Alpert et al. |
| 7,208,333 B2 | 4/2007 | Flanders et al. |
| 7,231,243 B2 | 6/2007 | Tearney et al. |
| 7,241,286 B2 | 7/2007 | Atlas |
| 7,366,562 B2 | 4/2008 | Dukesherer et al. |
| 7,414,779 B2 | 8/2008 | Huber et al. |
| 7,415,049 B2 | 8/2008 | Flanders et al. |
| 7,477,763 B2 | 1/2009 | Willis et al. |
| 7,605,681 B2 | 10/2009 | Wobben |
| 7,621,874 B2 | 11/2009 | Romley et al. |
| 7,625,366 B2 | 12/2009 | Atlas |
| 7,729,745 B2 | 6/2010 | Maschke |
| 7,751,865 B2 | 7/2010 | Jascob et al. |
| 7,785,261 B2 | 8/2010 | Maschke |
| 7,813,609 B2 | 10/2010 | Petersen et al. |
| 7,818,044 B2 | 10/2010 | Dukesherer et al. |
| 7,822,464 B2 | 10/2010 | Maschke et al. |
| 7,840,253 B2 | 11/2010 | Tremblay et al. |
| 7,848,791 B2 | 12/2010 | Schmitt et al. |
| 7,916,387 B2 | 3/2011 | Schmitt et al. |
| 7,935,060 B2 * | 5/2011 | Schmitt et al. ............ 600/467 |
| 8,162,834 B2 | 4/2012 | Feldman et al. |
| 8,214,010 B2 | 7/2012 | Courtney |
| 8,548,567 B2 | 10/2013 | Maschke |
| 2001/0031919 A1 | 10/2001 | Strommer et al. |
| 2002/0019644 A1 | 2/2002 | Hastings et al. |
| 2002/0049375 A1 | 4/2002 | Strommer et al. |
| 2002/0161351 A1 | 10/2002 | Samson et al. |
| 2005/0025797 A1 | 2/2005 | Wang et al. |
| 2005/0101859 A1 * | 5/2005 | Maschke ............ 600/427 |
| 2005/0113685 A1 | 5/2005 | Maschke et al. |
| 2005/0149002 A1 | 7/2005 | Wang et al. |
| 2005/0201662 A1 | 9/2005 | Petersen et al. |
| 2006/0025677 A1 | 2/2006 | Verard et al. |
| 2006/0084867 A1 | 4/2006 | Tremblay et al. |
| 2006/0095065 A1 | 5/2006 | Tanimura et al. |
| 2006/0100489 A1 | 5/2006 | Pesach et al. |
| 2006/0116577 A1 | 6/2006 | DeWitt |
| 2006/0173299 A1 | 8/2006 | Romley et al. |
| 2006/0241465 A1 | 10/2006 | Huennekens et al. |
| 2006/0241572 A1 | 10/2006 | Zhou |
| 2007/0038061 A1 | 2/2007 | Huennekens et al. |
| 2007/0060822 A1 | 3/2007 | Alpert et al. |
| 2007/0232933 A1 | 10/2007 | Gille et al. |
| 2007/0243137 A1 | 10/2007 | Hainfeld |
| 2008/0161696 A1 | 7/2008 | Schmitt et al. |
| 2008/0171937 A1 | 7/2008 | Dukesherer et al. |
| 2008/0177139 A1 | 7/2008 | Courtney et al. |
| 2008/0177183 A1 | 7/2008 | Courtney et al. |
| 2008/0180683 A1 | 7/2008 | Kemp |
| 2008/0269572 A1 | 10/2008 | Kanz et al. |
| 2008/0287795 A1 | 11/2008 | Klingensmith et al. |
| 2009/0018393 A1 | 1/2009 | Dick et al. |
| 2009/0043191 A1 | 2/2009 | Castella et al. |
| 2009/0174931 A1 | 7/2009 | Huber et al. |
| 2009/0195514 A1 | 8/2009 | Glynn et al. |
| 2009/0264768 A1 | 10/2009 | Courtney et al. |
| 2009/0299195 A1 | 12/2009 | Muller et al. |
| 2009/0306520 A1 | 12/2009 | Schmitt et al. |
| 2010/0076320 A1 | 3/2010 | Petersen et al. |
| 2010/0094127 A1 | 4/2010 | Xu |
| 2010/0210939 A1 | 8/2010 | Hartmann et al. |
| 2010/0253949 A1 | 10/2010 | Adler et al. |
| 2010/0274124 A1 | 10/2010 | Jascob et al. |
| 2011/0007315 A1 | 1/2011 | Petersen et al. |
| 2011/0058178 A1 | 3/2011 | Tearney et al. |
| 2011/0071404 A1 | 3/2011 | Schmitt et al. |
| 2011/0071405 A1 | 3/2011 | Judell et al. |
| 2011/0101207 A1 | 5/2011 | Schmitt |
| 2011/0151980 A1 | 6/2011 | Petroff |
| 2011/0157686 A1 | 6/2011 | Huber et al. |
| 2011/0172511 A1 | 7/2011 | Schmitt et al. |
| 2011/0178413 A1 | 7/2011 | Schmitt et al. |
| 2011/0190586 A1 | 8/2011 | Kemp |
| 2011/0216325 A1 | 9/2011 | Schmitt |
| 2011/0228280 A1 | 9/2011 | Schmitt et al. |
| 2012/0057157 A1 | 3/2012 | Petersen et al. |
| 2012/0236883 A1 | 9/2012 | Adler |
| 2012/0238869 A1 | 9/2012 | Schmitt et al. |
| 2012/0250028 A1 | 10/2012 | Schmitt et al. |
| 2012/0310081 A1 | 12/2012 | Adler et al. |
| 2013/0010303 A1 | 1/2013 | Petersen et al. |
| 2013/0012811 A1 | 1/2013 | Schmitt et al. |
| 2013/0023761 A1 | 1/2013 | Petroff |
| 2013/0051728 A1 | 2/2013 | Petroff |
| 2013/0072805 A1 | 3/2013 | Schmitt et al. |

FOREIGN PATENT DOCUMENTS

| | | |
|---|---|---|
| JP | 2004-290548 | 10/2004 |
| JP | 2006-006958 | 1/2006 |
| WO | 2008086613 | 7/2008 |
| WO | 2008086615 | 7/2008 |
| WO | 2008086616 | 7/2008 |
| WO | 2009009802 | 1/2009 |
| WO | 2009137659 | 11/2009 |

OTHER PUBLICATIONS

Translation of Office Action mailed from Japanese Patent Office on Oct. 22, 2013 for Japanese Patent Application No. 2009-536291 (4 pages).

Translation of Office Action mailed from Japanese Patent Office on Oct. 22, 2013 for Japanese Patent Application No. 2013-131070.

* cited by examiner

OPTO-ACOUSTIC IMAGING DEVICES AND METHODS

RELATED APPLICATIONS

This application is a continuation of U.S. patent application Ser. No. 13/051,567, filed on Mar. 18, 2011, now U.S. Pat. No. 8,449,468, which claims priority to and the benefit of U.S. patent application Ser. No. 11/983,417, filed on Nov. 8, 2007, now U.S. Pat. No. 7,935,060, which claims priority to and the benefit of U.S. Provisional Patent Application 60/857,573, filed on Nov. 8, 2006, the entire disclosures of each of which are herein incorporated by reference.

FIELD OF INVENTION

This invention relates to the field of optical imaging and more specifically to the design of fiber-optic probes for optical coherence tomography (OCT) and other optical imaging technologies, such as ultrasound.

BACKGROUND

In recent years, the underlying cause of sudden heart attacks (acute myocardial infarctions or AMI) has been the subject of much attention. The older prevailing theory of gradual occlusion of the coronary artery has been superseded by a new theory based on extensive histopathologic evidence that AMI is the result of a rupture in the coronary artery wall, specifically a rupture of a "vulnerable plaque." A vulnerable plaque, also known as Thin Capped Fibro-Artheroma (TCFA), is characterized by a thin fibrous cap covering a lipid pool located under the artery wall. Conventional x-ray based angiographic techniques can be used to detect narrowing of the artery. However, directly seeing the surface of the artery wall is essential to detect TCFA. Accordingly, a need therefore exists for a probe design that enables detecting and visualizing subsurface biological tissues and lipid pools.

SUMMARY OF THE INVENTION

The invention relates to methods and apparatus for imaging biological tissues and other materials using optical and acoustic imaging techniques. A combination of Optical Coherent Tomography (OCT), an interferometric imaging technology, and Intravascular Ultrasound (IVUS), is ideally suited to subsurface visualization of biological tissue, such as the artery wall, via small-diameter probes. The disclosed methods are based on a combination of IVUS (Intravascular ultrasound) and OCT (Optical Coherence Tomography) techniques that advantageously overcomes the weakness of each individual technique. In particular, the combination of both IVUS and OCT allows for a robust probe with many advantages.

IVUS is a medium-resolution (~100 um), medium-penetration (~2 cm) imaging technique. In contrast, OCT is a high-resolution (5-20 um), shallow-penetration (~1 mm) technique. Neither technique individually can detect the state of the arterial wall. For example, the cap thickness in a potentially hazardous TCFA can range from ~25 um to ~100 um. This range is within the measurement resolution of OCT, but beyond the measurement resolution of IVUS. Conversely, deep lipid pools beneath a thin cap greatly increases the risk of an AMI. OCT cannot be used to readily penetrate such deep lipid pools, but IVUS can readily be used to visualize such pools.

It is an object of the present invention to describe devices and methods whereby IVUS and OCT can be performed simultaneously. It is a further object of the invention to describe OCT optical sensors and IVUS ultrasound sensors that can be combined into the same catheter delivery system.

One advantage of the invention is the aligned nature of the OCT and ultrasound sensors such that co-registration of the cross-sectional images obtained by the two sensors can be obtained with high precision. Previous descriptions of such combined catheters did not provide the co-registration levels needed. Co-registration is important because coronary morphology changes rapidly, often in less than a millimeter of longitudinal distance.

It is another object of the invention to describe a sensor structure wherein two probe beams are orientated at substantially the same angle with respect to the longitudinal axis of the catheter. Again, this is to facilitate proper co-registration of the images. Differing launch angles of the probe beams implies that the two images diverge each other with depth. Computational correction of this divergence is complex and can lead to errors in image presentation.

It is another object of this invention to describe efficient methods of providing both optical and electrical energy to the rotating sensor assembly at the tip of the catheter. Using various torque wire and coated fibers to acts as co-axial signal lines saves valuable space within a catheter body.

It is a further object of the invention to describe mechanisms and configurations of the probe that will simultaneously reduce unwanted parasitic acoustical and optical back-reflections while still providing an aligned and otherwise functional probe assembly.

It is yet another object of the invention to describe efficient rotary mechanisms for coupling both electrical and optical energy simultaneously into the catheter.

It is another object of the invention to describe a combined probe utilizing capacitive micro-machined ultrasonic transducers (CMUT) to create a dual element probe such that both the ultrasound and optical beams focus on substantially the same tissue spot simultaneously.

In one aspect, the invention relates to a probe. The probe includes a sheath, a flexible, bi-directionally rotatable, optical subsystem positioned within the sheath, the optical subsystem comprises a transmission fiber, the optical subsystem capable of transmitting and collecting light of a predetermined range of wavelengths along a first beam having a predetermined beam size. The probe also includes an ultrasound subsystem, the ultrasound subsystem positioned within the sheath and adapted to propagate energy of a predetermined range of frequencies along a second beam having a second predetermined beam size. In one embodiment, a portion of the first and second beams scan the same region at different points in time. Alternatively, the first beam can be directed to scan a first band of a region that is substantially adjacent to a second band of the region, wherein the second beam scans the second band.

In another aspect, the invention relates to a system for medical examination. The system includes a first image processing device and a second image processing device. The system also includes a probe, in electrical communication with the first and second image processing devices. In turn, the probe includes a first sensor of are imaging system for optical coherence tomography having an optical fiber for directing and emitting light into an area adjacent to a catheter tip introduced into an examination area and for directing reflected light from the illuminated examination area to the first image processing device; and a second sensor of an intravascular ultrasound imaging system for transmitting and receiving acoustic signals to a second image processing device as electrical signals. Further, the system also includes a display device for outputting of images processed by the first and the second image processing devices.

In yet another aspect, the invention relates to an imaging probe adapted for insertion in a lumen. The probe includes a sheath having a core and an endface, an optical subsystem having an optical focus, the optical subsystem positioned within the core; and an array of ultrasound transducers having an acoustic focus, the array disposed on a portion of the endface.

In still another aspect, the invention relates to a probe. The probe includes a sheath, a first ultrasound subsystem, the first ultrasound subsystem positioned within the sheath and adapted to propagate energy along a first vector, and a second ultrasound subsystem, the second ultrasound subsystem positioned within the sheath and adapted to propagate energy along a second vector, wherein the first and second vectors are substantially parallel and opposite in direction.

In yet another aspect, the invention relates to a method of imaging a tissue region. The method includes the steps of inserting a combination ultrasound and OCT imaging probe in a lumen, and performing ultrasound imaging, and then performing optical coherence tomography imaging. In one embodiment of this method a flush solution is applied during the optical coherence tomography imaging. In another related method of this aspect, the ultrasound imaging is performed simultaneously with the optical coherence tomography imaging.

In still another aspect, the invention relates to a method of imaging a tissue region, the method comprising the steps of inserting a combination ultrasound and OCT imaging probe in a lumen, performing ultrasound imaging simultaneously with optical coherence tomography imaging whereby a flush solution is applied during the imaging.

Additional aspects of the invention include methods of fabricating probes that include sensor arrays, wherein each sensor includes an ultrasound transducer and a driver.

It should be understood that the terms "a," "an," and "the" mean "one or more," unless expressly specified otherwise.

The foregoing, and other features and advantages of the invention, as well as the invention itself, will be more fully understood from the description, drawings, and claims which follow.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. The drawings associated with the disclosure are addressed on an individual basis within the disclosure as they are introduced.

The claimed invention will be more completely understood through the following detailed description, which should be read in conjunction with the attached drawings. In this description, like numbers refer to similar elements within various embodiments of the present invention.

DETAILED DESCRIPTION OF THE INVENTION

The following description refers to the accompanying drawings that illustrate certain embodiments of the present invention. Other embodiments are possible and modifications may be made to the embodiments without departing from the spirit and scope of the invention. Therefore, the following detailed description is not meant to limit the present invention. Rather, the scope of the present invention is defined by the appended claims.

It should be understood that the order of the steps of the methods of the invention is immaterial so long as the invention remains operable. Moreover, two or more steps may be conducted simultaneously or in a different order than recited herein unless otherwise specified.

Figure 1A:
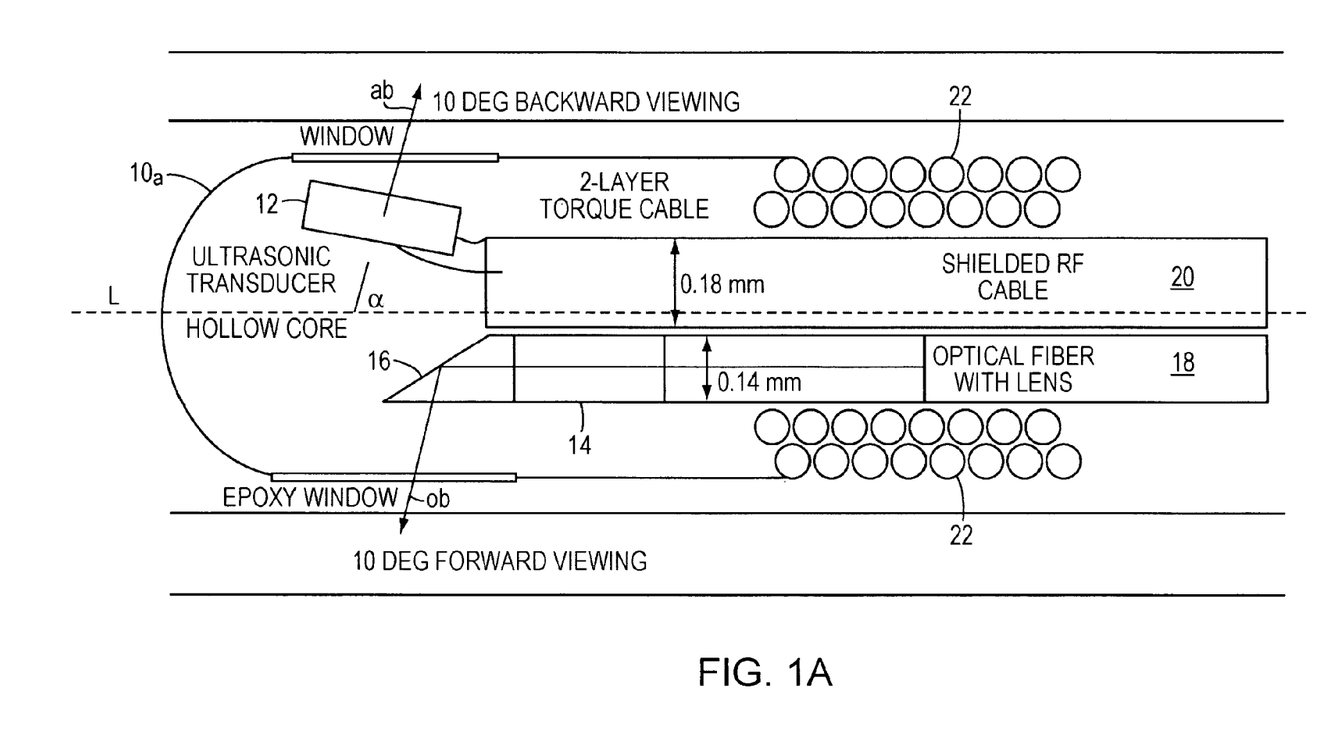
FIG. 1A depicts a cross-sectional view of a longitudinally aligned IVUS/OCT probe according to an illustrative embodiment of the invention.

FIG. 1A illustrates a portion of an imaging probe 10a, using a conventional IVUS ultrasonic transducer 12, an optical transducer 14 which includes an angled-tip optical lens assembly 16 attached to a single mode fiber 18, a standard miniature RF cable 20 delivering power to the IVUS ultrasonic transducer, and a torque cable 22 providing a stable revolution rate to the assembly.

Torque cables are generally preferred in this dual probe catheter as the optical fiber is known to have a very low torsional (rotational) stiffness. For example, a 1 cm length of standard telecomm fiber 125 µm in diameter with approximately 1 millionth of a N-m of applied torque will twist one degree. Therefore, it is unrealistic to expect the fiber to be sufficiently torsionally rigid to drive the complete assembly.

In FIG. 1A, both the optical transducer 12 and the IVUS ultrasonic transducer 14 are angled to minimize unwanted parasitic reflections from reaching the respective transducers, and to create an aligned cross-sectional "cut" through the tissue. As shown, the acoustic beam (ab) emanating from the transducer is parallel to optical beam (ob) emanating from the fiber. The direction of these two parallel beams is rotated by an angle α relative to the longitudinal axis of the probe. As shown in the figure, a small amount of longitudinal displacement is acceptable.

As a first order approximation, this allowable displacement is the approximate maximum beam width of the combined probe 10a. In most cases, this will be the width of the ultrasound beam, which typically has a width of ~100 to 300 um (the OCT beam width is typically 25 um). Keeping the longitudinal displacement below this longitudinal displacement limit ensures the beams remain overlapped. Furthermore, having the two beams at 180 degrees opposite to each other ensures easier real-time or post-processing alignment of the two images for an overlay display.

Figure 1B:
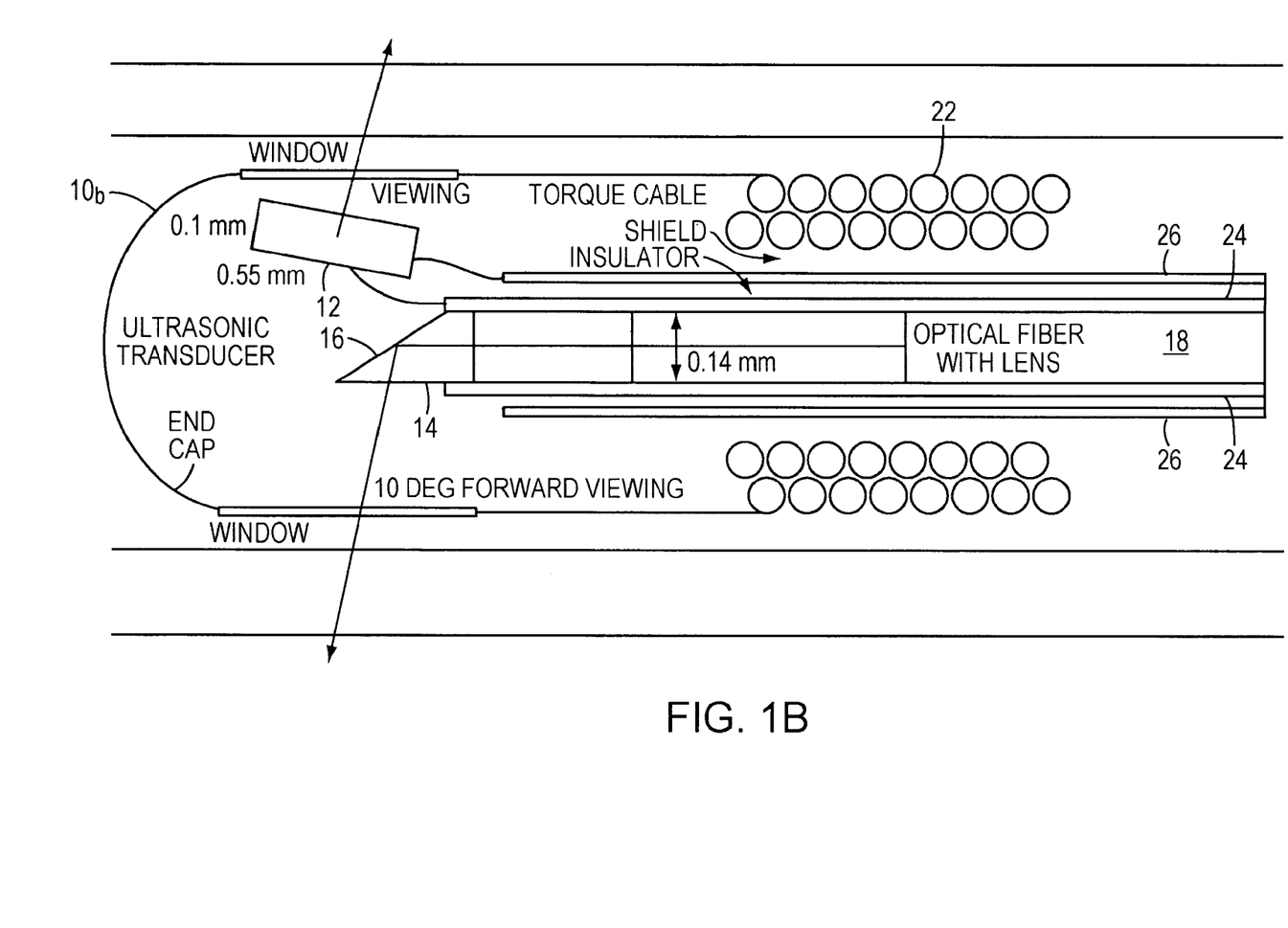
FIG. 1B depicts a probe utilizing a metal coated fiber with a shield tube according to an illustrative embodiment of the invention.

FIG. 1B depicts a probe 10b for imaging whereby the overall diameter is reduced. Here, a metal coated fiber 24 is shown inside an insulated tube 26. These two cylindrical surfaces (tube and coating), the dielectric constant of the insulation, and the insulation thickness can be configured to form a simple coaxial transmission line for the RF signals. Such RF signals may vary from 10 to 60 MHz depending on the IVUS ultrasonic transducer design.

Figure 1C:
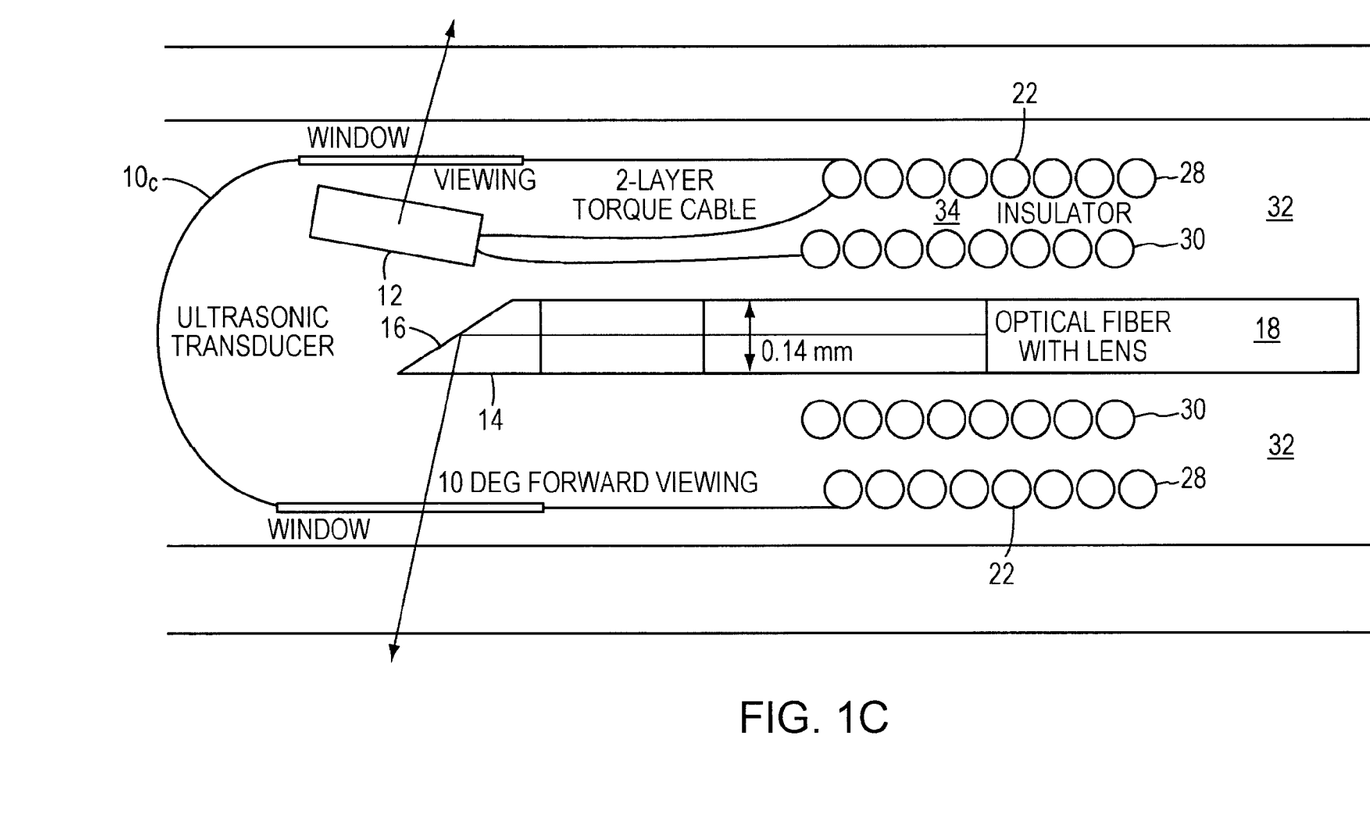
FIG. 1C depicts a probe utilizing the coils of the torque cable assembly as conductors according to an illustrative embodiment of the invention.

FIG. 1C illustrates another probe embodiment 10c with a different conduction mechanism. Specifically, in the probe 10c shown, the inner inner 28 and outer 30 coils of a torque cable 22 form a coaxial transmission line 32. An insulated spacer 34 is inserted between the inner and outer coils to prevent a short circuit condition. The embodiment shown in FIG. 1C allows RF power to be transmitted using an integral torque wire. In one embodiment, the transducer is coated with epoxy. In one embodiment, both the ultrasound transducer and the optical fiber rotate together, being driven by the same torque wire. The distal tip epoxy encases the optical fiber, the ultrasound transducer and its associated supply wires. Hence, the epoxy is selected for suitable optical and acoustic properties, as well as the required electrical insulation. Various epoxies and silicon compounds can be purchased and/or specifically tailored that meet these requirements.

Figure 1D:
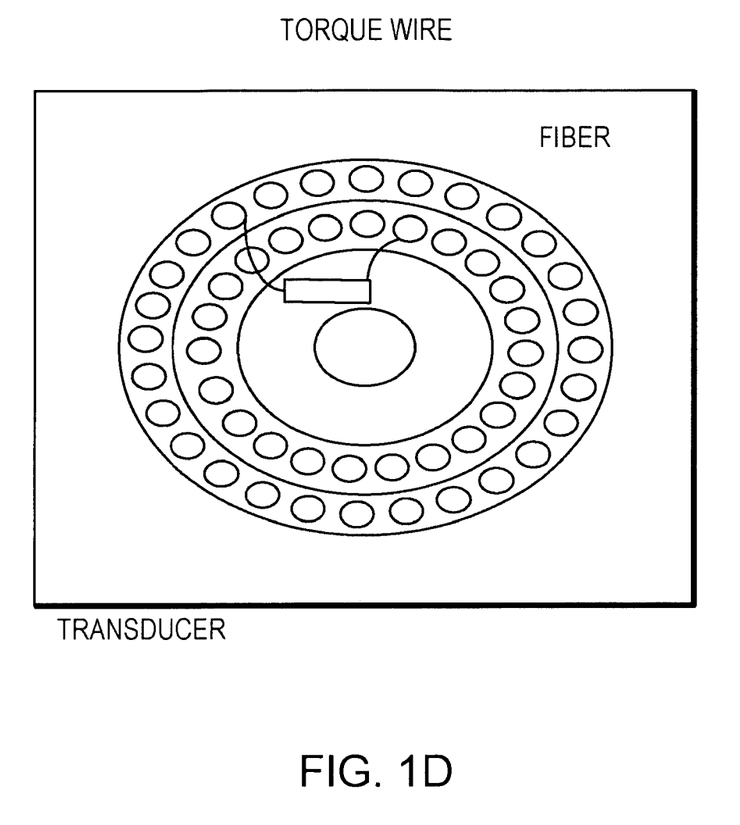
FIG. 1D depicts a cross-sectional view of the probe embodiment depicted in FIG. 1C.

FIG. 1D illustrates a cross-section of the embodiment of FIG. 1C. The two wires connected to the transducer shown in FIGS. 1C and 1D are rigid and rotate with the transducer.

Figure 1E:
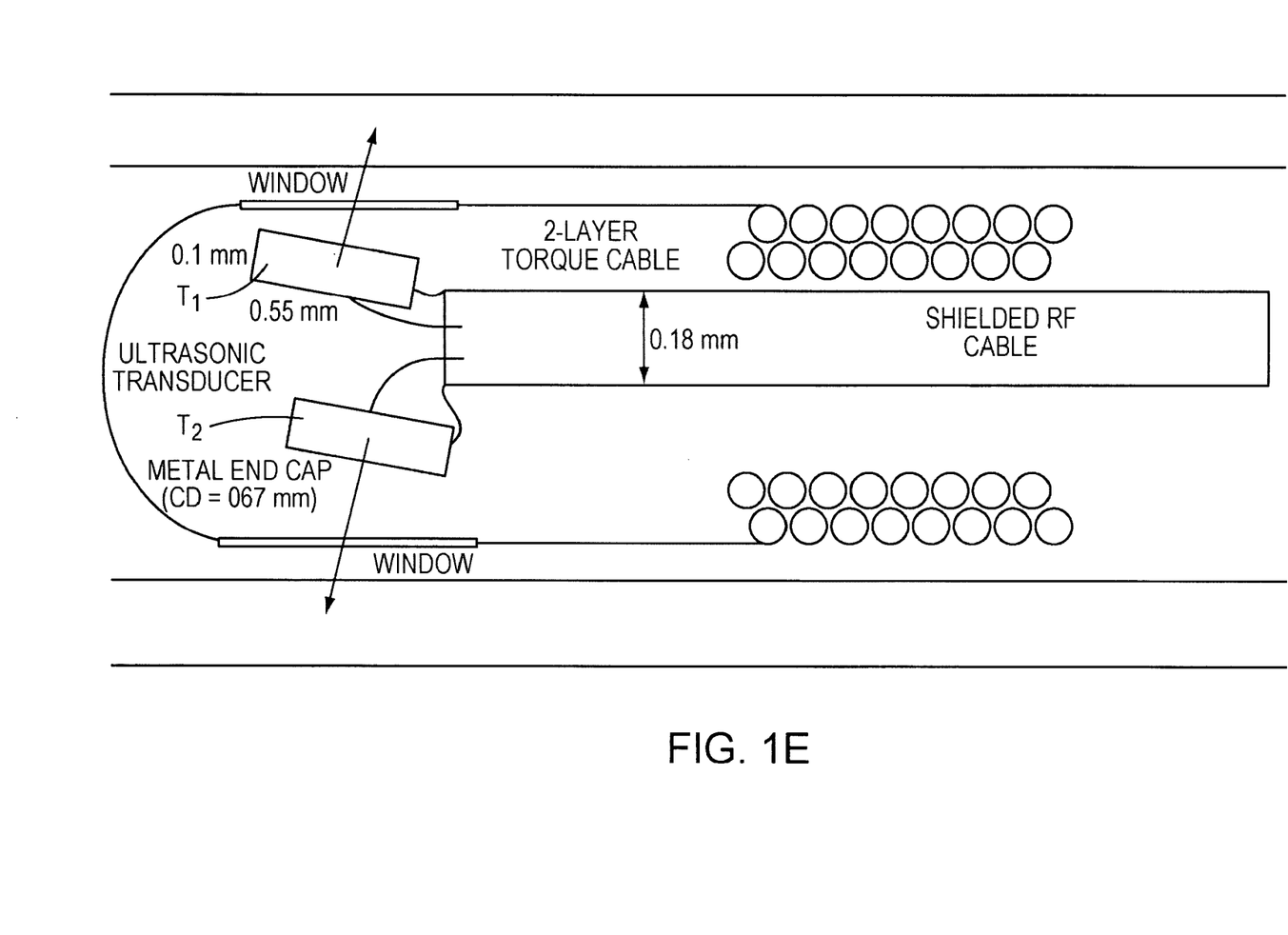
FIG. 1E depicts a probe that includes two transducers adapted for operating at different frequencies according to an illustrative embodiment of the invention.

FIG. 1E illustrates another optical probe embodiment wherein two IVUS ultrasonic transducers $T_1$, $T_2$ operating at different frequencies are integrated in the device. The lower frequency transducer $T_1$ allows for ultrasound with s deeper scanning range, but lower resolution. Conversely, the higher frequency $T_2$ transducer allows for ultrasound with increased resolution but less depth penetration. In one embodiment, one transducer operates at about 5 MHz and the other transducer operates at about 60 MHz. By using transducers with differing frequency ranges, an optical probe gains the advantages of both transducers, and mitigates disadvantages of each transducer, respectively. This dual transducer probe achieves the same overall goals as the combined OCT/IVUS catheter in the case where very high resolution (~10 um, OCT) is not needed in favor of very high penetration (~3-5 cm) offered by a lower frequency ultrasound transducer.

Figure 2:
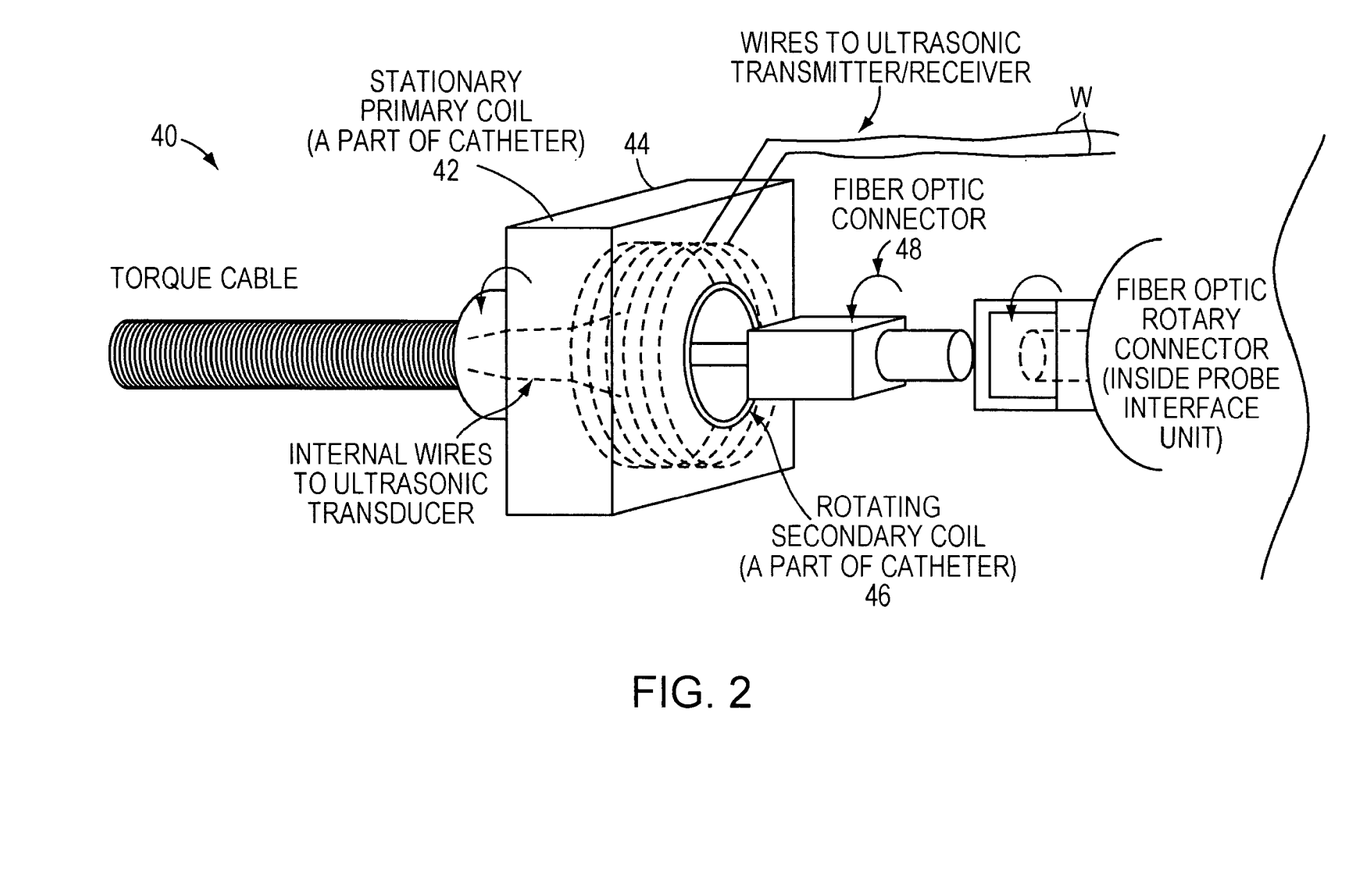
FIG. 2 depicts a rotating coupling mechanism for delivering both RF and optical energy to a rotating probe assembly according to an illustrative embodiment of the invention.

FIG. 2 depicts a probe embodiment 40 that incorporates a mechanism for transmitting both RF energy and optical energy to the rotating assembly. Specifically, a transformer scheme is used wherein a first coil 42 is attached to the rotating assembly 44, and a second coil 46 is integrated with the connector 48 of the optical probe. This configuration has the advantage that both coils move with the assembly during a 'pull-back' (longitudinal) scan operation. Such pullbacks are used in both OCT and IVUS scans. When coupled with a rotation, a spiral scan pattern is created inside the arterial lumen. However, this approach results in an increased cost for a one-time-use catheter.

Figure 3:
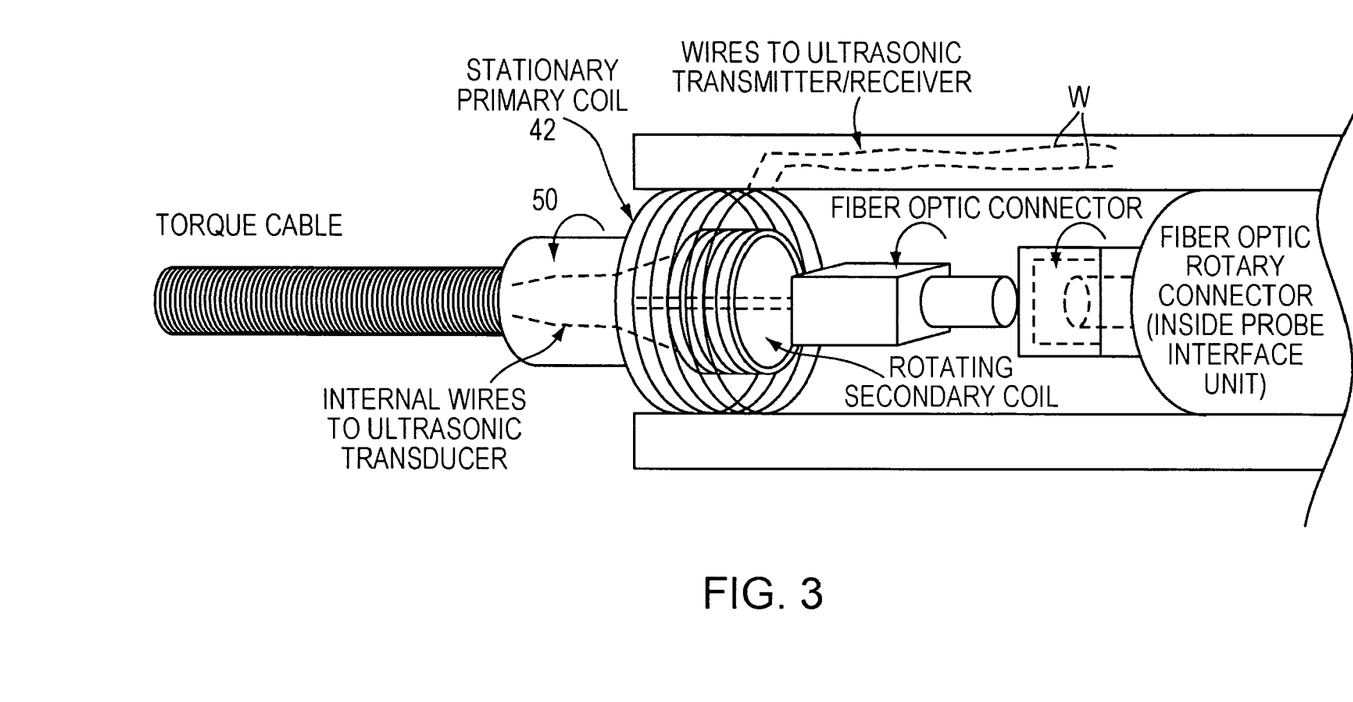
FIG. 3 depicts a rotating coupling mechanism wherein the stationary coil is part of the probe interface unit according to an illustrative embodiment of the invention.

FIG. 3 illustrates an alternative coupling scheme wherein the fixed coil 42 is part of the drive unit 50 (motorized assembly providing rotational and longitudinal motions). In this embodiment, the fixed coil is permanent, and must be long enough to efficiently couple the RF energy into the rotating catheter coil over the entire pullback length. Although incorporating the fixed coil to the drive unit imposes additional requirements to the drive electronics, the decrease in catheter usage provides an overall cost savings.

Currently, conventional slip-ring technology is widely used in the field of optical imaging. Alternatively to FIGS. 2 and 3, slip-ring technology can be used in IVUS probes described herein. However, for a probe with a centered optics configuration, the slip-ring is more difficult to manufacture than in the IVUS-only case.

Figure 4:
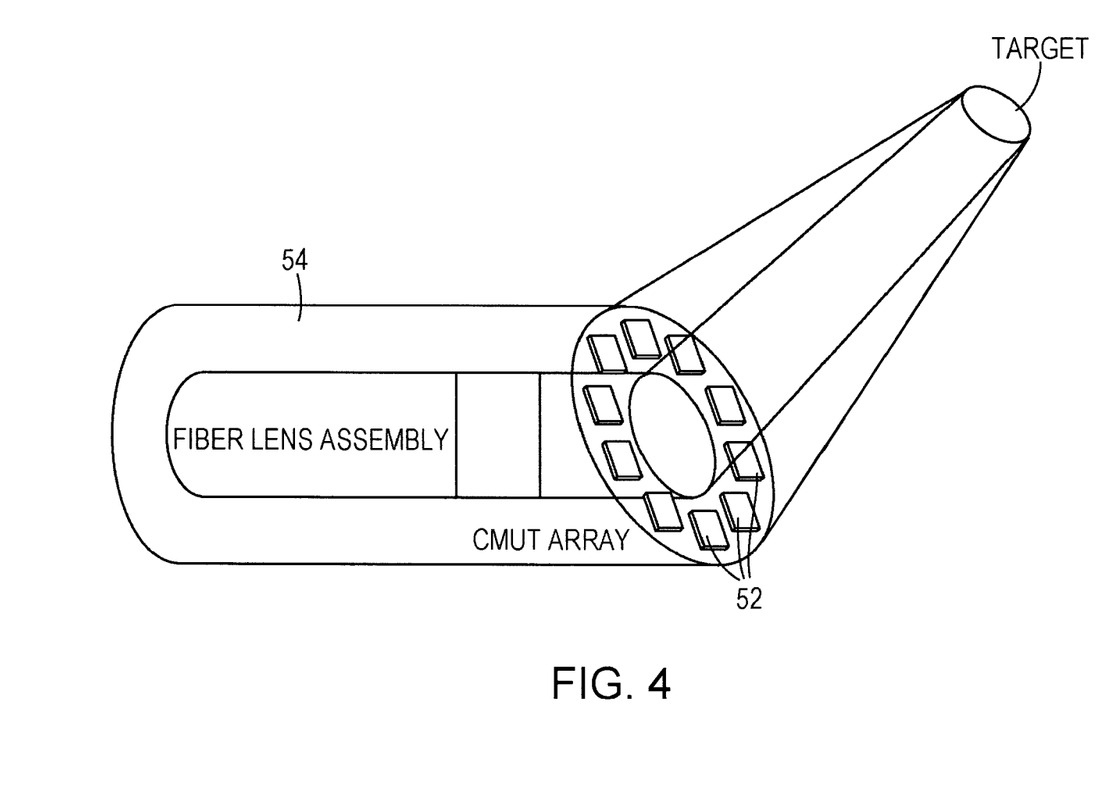
FIG. 4 depicts a probe tip wherein CMUT technology is employed to achieve a dual focused beam according to an illustrative embodiment of the invention.

FIG. 4 illustrates an embodiment that includes capacitive micro-machined ultrasonic transducers (CMUT) 52 integrated in a coronary imaging probe 54. The advantage of the CMUT is the small size of the transducer, which is fabricated via conventional electronic CMOS processes. The small size and photolithographic fabrication allows customized arrays of transducers to be built with the drive electronics on the same substrate. In this example, an array is formed in an annular region around the optical transducer. As a result, a co-focused, aligned and combined beam can be formed, which eliminates the need for software registration and removes a potential source of error. However, this probe tip may be larger than the embodiment shown in FIG. 1.

Figure 5A:
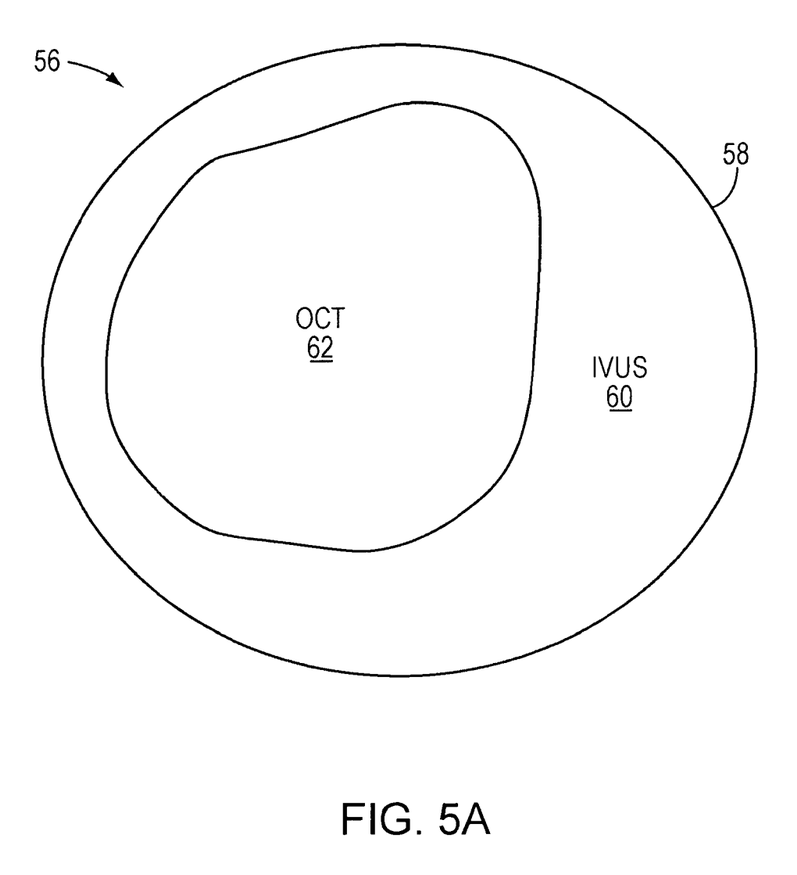
FIG. 5A depicts a fused OCT-IVUS schematic according to an illustrative embodiment of the invention.

FIG. 5A illustrates a fused OCT-IVUS image 56, wherein the demarcation line 58 is chosen near the OCT penetration limit. As shown, by registering the relative images of the ultrasound 60 and the OCT scans 62, it is possible for a clinician to view a composite image that shows additional physiological data. This approach can be used to image subsurface lipid pools.

Figure 5B:
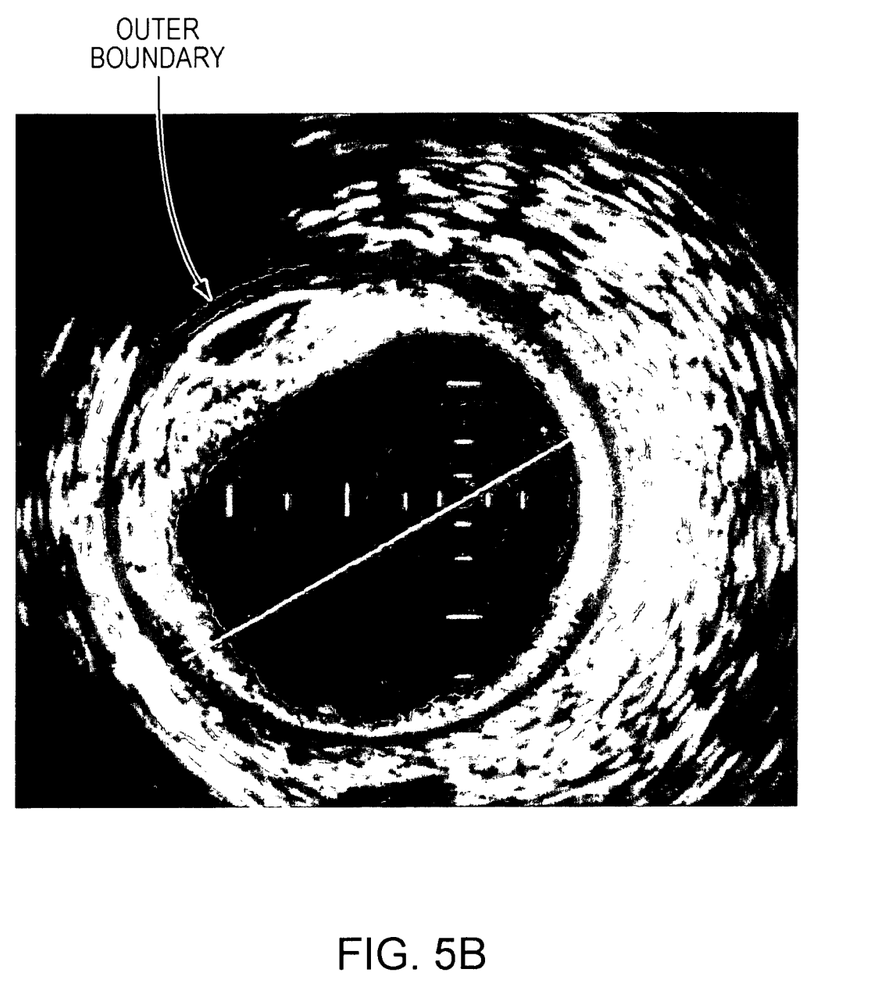
FIG. 5B depicts a fused OCT-IVUS image according to an illustrative embodiment of the invention.

FIG. 5B illustrates a fused OCT/IVUS image wherein the OCT portion appears in the image center and the IVUS portion appears in the periphery. The outer boundary indicates approximately the boundary where the two regions intersect.

Not shown in the embodiments depicted in the figures is a guide catheter. Typically, the guide catheter is a larger bore catheter used to introduce the smaller imaging catheter into the main arterial trunk. From the guide catheter, a flush solution can be expelled to create a clear, blood-free imaging region when OCT imaging is performed. Alternative embodiments may include a flush lumen within the imaging catheter whereby the flush solution is ejected at the imaging tip rather than from the guide catheter.

The aspects and embodiments of the invention can incorporate various components of varying dimension and materials as is known to one of ordinary skill. Various specific dimensions and materials are described herein, however, these exemplary materials are not meant to be limiting, but only to evidence additional more specific embodiments. For all of the measurements discussed below, the dimension given also includes a range of greater than about 10-20% of the dimension given and less than about 10%-20% of the dimension given. In addition, for all of the measurements discussed below, the dimension given also includes a range of greater than about 20-50% of the dimension given and less than about 20%-50% of the dimension given. Further, in addition, for all of the measurements discussed below, the dimension given also includes a range of greater than about 50-100% of the dimension given and less than about 50%-100% of the dimension given.

In one probe embodiment, the viewing window used is a transparent epoxy-based window. Further, in another embodiment, the transducers used have a first dimension of about 0.1 mm and a second dimension of about 0.5 mm. The forward viewing angle is about 10 degrees in one embodiment of the probe. The end-cap used in one probe embodiment includes a metal. The probe can include a hollow core that is substantially filled with an epoxy material in some embodiments. In one embodiment, the width of the shield RF cable is about 0.18 mm.

It should be appreciated that various aspects of the claimed invention are directed to subsets and substeps of the techniques disclosed herein. Further, the terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed. Accordingly, what is desired to be secured by Letters Patent is the invention as defined and differentiated in the following claims, including all equivalents.

What is claimed is:

1. An intravascular imaging system comprising:
    a first image processing device;
    a second image processing device;
    a probe, in electrical communication with the first and second image processing devices, the probe comprising
        a rotatable optical fiber;
        a torque wire, the rotatable optical fiber disposed in the torque wire;
        a first coil;
        a second coil, wherein the first coil and the second coil are disposed at a proximal end of the probe;
        a probe tip comprising
            an angled optical assembly in optical communication with the rotatable optical fiber and the first image processing device; and
            an ultrasound transducer in electrical communication with the first coil and the second image processing device wherein a portion of the rotatable optical fiber is disposed in the first coil;
    a fiber optic connector coupled to the rotatable optical fiber; and
    a display device for outputting of images processed by the first and the second image processing devices.

2. The system according to claim 1, wherein the display device is adapted to jointly display the images processed by the first and the second image processing devices.

3. The system according to claim 2, wherein the display device is adapted to display an image generated by the first image processing device in a center area on a screen of the display device, and display an image generated by the second image processing device in an outer area on the screen of the display device.

4. The system of claim 1 further comprising a probe interface unit comprising a fiber optic rotary connector positioned to couple with the fiber optic connector.

5. The system of claim 1 further comprising a sheath, the probe disposed in the sheath.

6. The system of claim 1 wherein the fiber optic connector is concentrically disposed relative to the first coil.

7. A method of imaging a blood vessel comprising:
    providing a rotatable probe comprising an ultrasound sensor, an optical coherence tomography sensor, a first coil, and a second coil;
    coupling electrical energy from a first coil to a second coil;
    coupling electrical energy to the ultrasound sensor from the second coil;
    performing ultrasound imaging such that a first set of image data is collected with respect to the blood vessel using a first beam from the ultrasound sensor oriented at a first angle,
    performing optical coherence tomography imaging such that a second set of image data is collected with respect to the blood vessel using a second beam from the optical coherence tomography sensor oriented a second angle; and
    co-registering cross-sectional images of the blood vessel generated using the first set of image data and the second set of image data.

8. The method of claim 7 further comprising the step of orienting the first beam and the second beam such that the first angle and the second angle are equal.

9. The method of claim 8 further comprising displaying one or more co-registered cross-sectional images of the blood vessel.

10. The method of claim 9 further comprising displaying a composite image that includes physiological data and one or more co-registered cross-sectional images of the blood vessel.

11. The method of claim 10 wherein the physiological data includes a subsurface lipid pool.

12. The method of claim 7 wherein co-registering the cross-sectional images includes selecting a boundary corresponding to an intersection of the first set of image data and the second set of image data.

13. The method of claim 12 further comprising setting the boundary substantially near an optical coherence tomography penetration limit.

14. The method of claim 7 further comprising collecting the second set of image data along a spiral pattern traced with respect to the blood vessel.

* * * * *